(12) United States Patent
Akhavan et al.

(10) Patent No.: US 12,178,705 B2
(45) Date of Patent: Dec. 31, 2024

(54) GLENOID AUGMENTATION USING SOFT TISSUE GRAFT

(71) Applicant: Arthrex, Inc., Naples, FL (US)

(72) Inventors: Sam Akhavan, Wexford, PA (US); Thomas Dooney, Jr., Naples, FL (US); Loren D. Crook, Fort Myers, FL (US)

(73) Assignee: Arthrex, Inc., Naples, FL (US)

( * ) Notice: Subject to any disclaimer, the term of this patent is extended or adjusted under 35 U.S.C. 154(b) by 189 days.

(21) Appl. No.: 17/516,316

(22) Filed: Nov. 1, 2021

(65) Prior Publication Data

US 2023/0139844 A1  May 4, 2023

(51) Int. Cl.
| | | |
|---|---|---|
| *A61B 17/04* | (2006.01) | |
| *A61B 7/04* | (2006.01) | |
| *A61F 2/00* | (2006.01) | |
| *A61F 2/08* | (2006.01) | |
| *A61F 2/30* | (2006.01) | |
| *A61F 2/40* | (2006.01) | |
| *A61L 27/36* | (2006.01) | |

(52) U.S. Cl.
CPC ...... *A61F 2/30734* (2013.01); *A61B 17/0401* (2013.01); *A61F 2/4081* (2013.01); *A61L 27/3604* (2013.01); *A61L 27/3641* (2013.01); *A61F 2002/30736* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 8,317,829 B2 | 11/2012 | Foerster et al. | |
| 8,562,647 B2 * | 10/2013 | Kaiser ................ | A61B 17/0401 |
| | | | 606/232 |
| 8,597,336 B2 * | 12/2013 | van Der Burg ....... | A61F 2/0811 |
| | | | 606/300 |
| 8,668,718 B2 * | 3/2014 | Euteneuer ............ | A61B 17/068 |
| | | | 606/219 |
| 9,149,267 B2 * | 10/2015 | Norton ................ | A61B 17/0401 |
| 9,220,516 B2 * | 12/2015 | Lang ................... | A61B 17/1703 |
| | (Continued) | | |

FOREIGN PATENT DOCUMENTS

| | | | |
|---|---|---|---|
| EP | 3753497 A1 * | 12/2020 | ............. A61B 17/04 |
| WO | WO-2017136396 A1 * | 8/2017 | ......... A61B 17/0401 |

OTHER PUBLICATIONS

Drake Medical Plastics, "Why PEEK is an Ideal Dental Material", entire document, Nov. 26, 2020.

(Continued)

*Primary Examiner* — Ann Schillinger
(74) *Attorney, Agent, or Firm* — Potomac Law Group, PLLC

(57) ABSTRACT

Surgical constructs, assemblies, kits and methods of tissue fixation are disclosed. Glenoid augmentation is conducted with one or more soft tissue grafts placed on the anterior glenoid to fill a glenoid defect. Knotted or knotless suture anchors can deliver and fixate the soft tissue graft within the glenoid bone defect. Suture anchors can also secure the native ligament to the soft tissue graft and provide stability to the shoulder joint. Soft suture anchors can deliver and fixate a soft tissue graft within the bone defect. The native soft tissue can be repaired over top of the soft tissue graft into its anatomical position.

8 Claims, 3 Drawing Sheets

(56) References Cited

U.S. PATENT DOCUMENTS

| | | | | |
|---|---|---|---|---|
| 9,451,973 | B2* | 9/2016 | Heilman | A61B 17/1778 |
| 9,554,910 | B2* | 1/2017 | Vanasse | A61F 2/28 |
| 9,693,765 | B2* | 7/2017 | Sullivan | A61B 17/842 |
| 10,022,118 | B2* | 7/2018 | Norton | A61B 17/16 |
| 10,076,377 | B2* | 9/2018 | Bonutti | A61B 17/12131 |
| 10,314,688 | B2* | 6/2019 | Shepard | A61L 27/54 |
| 10,610,211 | B2* | 4/2020 | Callison | A61B 17/0401 |
| 10,813,742 | B2* | 10/2020 | Adams | A61B 17/3423 |
| 11,076,865 | B2 | 8/2021 | Ng et al. | |
| 11,344,288 | B2* | 5/2022 | Beaulier | A61B 17/0401 |
| 11,484,401 | B2* | 11/2022 | Whittaker | A61L 27/24 |
| 11,559,402 | B2* | 1/2023 | Sengun | A61F 2/30749 |
| 11,771,416 | B2* | 10/2023 | Dooney, Jr. | A61B 17/0401 606/144 |
| 11,957,566 | B2* | 4/2024 | Bonner | A61L 27/50 |
| 2006/0149370 | A1* | 7/2006 | Schmieding | A61F 2/08 623/13.11 |
| 2008/0188936 | A1* | 8/2008 | Ball | A61F 2/08 623/13.13 |
| 2008/0281422 | A1* | 11/2008 | Schmieding | A61F 2/30756 606/228 |
| 2009/0306776 | A1 | 12/2009 | Murray | |
| 2013/0144335 | A1 | 6/2013 | Sandow | |
| 2017/0095324 | A1* | 4/2017 | Adams | A61F 2/08 |
| 2018/0028173 | A1 | 2/2018 | Dooney et al. | |
| 2018/0206977 | A1 | 7/2018 | Park et al. | |
| 2018/0263755 | A1* | 9/2018 | Adams | A61B 17/0401 |
| 2019/0290420 | A1 | 9/2019 | Dougherty et al. | |
| 2020/0086000 | A1* | 3/2020 | Elian | A61L 27/54 |
| 2020/0261072 | A1 | 8/2020 | Beaulier et al. | |
| 2020/0315677 | A1 | 10/2020 | Hachem et al. | |
| 2021/0113343 | A1 | 4/2021 | Ponce et al. | |
| 2021/0236289 | A1 | 8/2021 | Sengun et al. | |
| 2021/0251741 | A1 | 8/2021 | Bonner et al. | |

OTHER PUBLICATIONS

International Search Report and Written Opinion for International Application No. PCT/US2022/040286, dated Nov. 30, 2022.

Ogimoto et al., "Arthroscopic glenoid reconstruction for glenoid bone loss in recurrent anterior glenohumeral Instability, using osteochondral autograft from the contralateral lateral femoral condyle: a new technique and case report," JSES Open Access, 2018, vol. 2, pp. 104-108, Elsevier, Amsterdam, Netherlands.

* cited by examiner

GLENOID AUGMENTATION USING SOFT TISSUE GRAFT

BACKGROUND

The present disclosure relates to the field of surgery and, more particularly, to constructs, systems, kits and methods for reconstructive surgeries.

SUMMARY

Surgical constructs, assemblies, and kits are disclosed. Glenoid augmentation is achieved with one or more soft tissue grafts that are placed on the anterior glenoid, to fill a glenoid defect or to just simply increase glenoid stability. Suture anchors can deliver and fixate soft tissue grafts within the bone defect or at a glenoid surface. Suture anchors can secure native ligament to the soft tissue grafts and provide stability to the shoulder joint. Native soft tissue can be repaired over top of the soft tissue grafts into its anatomical position. Suture anchors can be knotless or knotted. Suture anchors can be soft suture anchors.

Methods of surgeries are also disclosed. In an embodiment, a method of grafting is conducted with soft tissue grafts that fill a glenoid defect and replace the bone loss. In an embodiment, a method of grafting is conducted with soft tissue grafts that are secured to the glenoid, to augment the glenoid and add glenoid stability.

DETAILED DESCRIPTION

Figure 1:
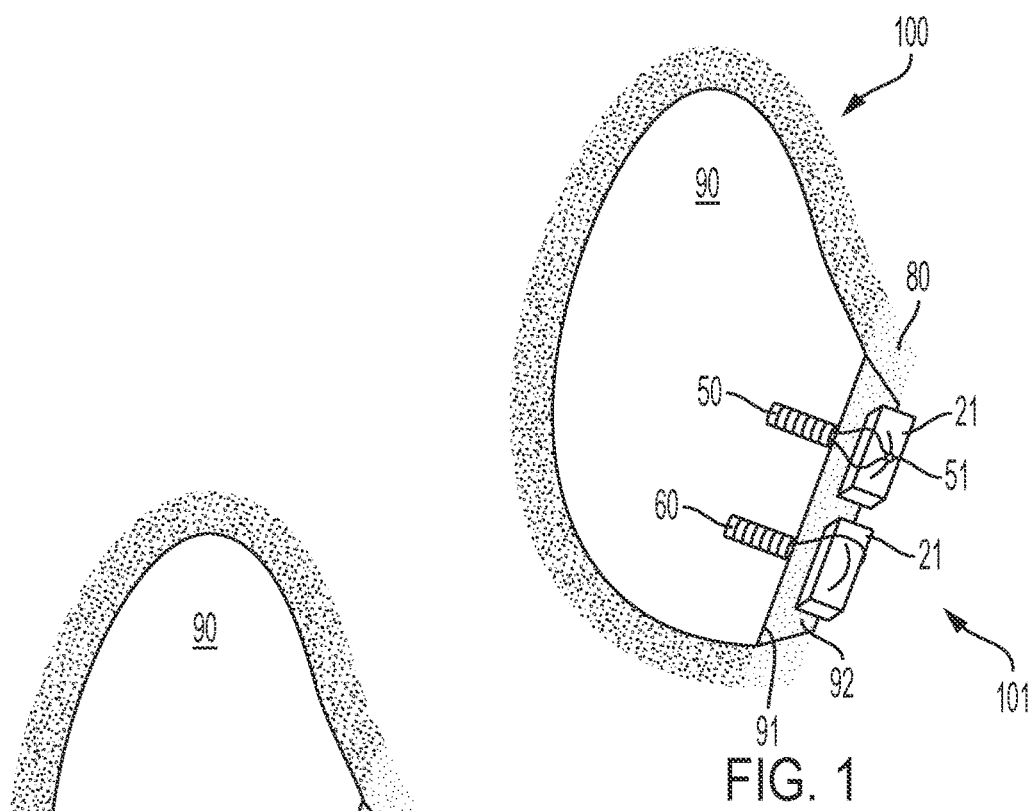
FIG. 1 illustrates an exemplary glenoid augmentation with soft tissue graft.

The present disclosure provides methods, surgical constructs, assemblies, kits and repair systems for soft tissue graft insertion and positioning on the anterior glenoid, to fill glenoid bone loss and/or to reinforce the glenoid for additional glenoid stability.

Glenoid augmentation is achieved with one or more soft tissue grafts placed on the anterior glenoid to fill a glenoid defect or to simply augment the glenoid to provide added glenoid stability. Suture anchors can deliver, position, fixate and secure the soft tissue grafts at the glenoid defect, to fill in the defect, or onto the glenoid. Suture anchors can also secure the native ligament to the soft tissue graft to provide additional stability to the shoulder joint. The native soft tissue can be repaired over top of the soft tissue graft into its anatomical position. Suture anchors can be knotless or knotted.

A repair system includes one or more soft tissue grafts and fixation devices provide with flexible strands that deliver and secure the one or more soft tissue grafts to the glenoid. The repair system eliminates metal cerclage and cabling (metal wires, cables, etc.) as well as metal components (metal fittings, screws, buttons, suture-button constructs, etc.). The techniques improve the bone loss in traumatic glenohumeral dislocation or chronic glenohumeral dislocation/subluxation by delivering and fixating pre-shaped and pre-dimensioned soft tissue grafts at the glenoid defect, or onto the glenoid, with fixation devices such as knotted or knotless anchors.

In an embodiment, a soft tissue glenoid repair system includes knotless and/or knotted suture anchors to secure one or more soft tissue grafts (optionally with the native labrum) to the glenoid or within a glenoid bone defect. The soft tissue grafts can be folded one to several times to alter the shape of the total graft construct. In addition, the soft tissue grafts do not extend laterally beyond the glenoid rim in order to contact the glenoid to reduce abnormal motion. Further, the native labrum can be tied down to the soft tissue grafts so that the labrum will contact the glenoid to keep it stable and in place.

Using soft tissue grafts in lieu of bone blocks/bone grafts for glenoid repairs makes it much easier to deliver and fixate the grafts without the risk of further harm to the shoulder joint. Current bone loss procedures utilize bone grafts using screws and other rigid fixation techniques to resolve the bone loss and gain stability. These techniques are difficult to undergo, have a high revision rate, and could cause further damage to the shoulder. The repair systems and glenoid augmentation methods of the present disclosure eliminate all metal/rigid fixation devices and components, by providing a simple and compact design, and strong and stable fixation. The soft tissue glenoid repair construct is a flexible, tensionable construct that eliminates the need for metal components and bone block grafts in a glenoid loss repair.

Soft tissue glenoid repair constructs, systems, assemblies, kits and methods of glenoid repairs are disclosed. A soft tissue glenoid repair construct can create a repair without metal cerclage and cabling (metal wires, cables, etc.) and/or metal components (metal fittings, screws, buttons, suture-button constructs, etc.). A soft tissue glenoid repair construct includes one or more soft tissue grafts that are positioned to fill a glenoid bone loss. Glenoid bone loss is a common orthopedic finding where a portion of the glenoid is no longer present. This loss of bone results in instability between the humeral head and the glenoid, resulting in pain to the patient and further orthopedic complications.

A surgical construct includes one or more soft tissue grafts which can be introduced via the rotator interval to lie on the surface of the glenoid at the defect site (the glenoid bone loss) to fill the loss. The glenoid defect consists of the glenoid with bone loss, typically represented by a surface which is about perpendicular to the face of the glenoid (the glenoid defect is a 3-D space adjacent the labrum). The soft tissue grafts can have various forms and configurations and can be folded several times to fill in the glenoid loss and provide stability to the shoulder joint. The glenoid augmentation of the present disclosure eliminates grafting of the glenoid with iliac crest, allograft, distal tibia, coracoid transfer, etc. The glenoid augmentation enables the simple delivering, positioning, and fixation of the soft tissue graft with associated graft suture anchors, as well as the fixation of the native soft tissue on top of the soft tissue graft to repair the native soft tissue into its anatomical position. The constructs and methods of the present disclosure allow for precise and fast placement of a graft without additional incisions and unnecessary drilling of bone tunnels through the bone to be grafted (glenoid), as well as improved suture management at the glenoid repair site.

Methods of surgeries are also disclosed. An exemplary method includes inter alia the steps of: (i) positioning one or more soft tissue grafts into a glenoid defect (glenoid bone loss); and (ii) securing, with at least one suture anchor, the one or more soft tissue grafts to the glenoid defect to fill the defect. The method can further include the steps of: attaching the one or more soft tissue grafts to the at least one suture anchor; inserting the at least one suture anchor attached to the soft tissue grafts into the glenoid; and delivering and fixating the one or more soft tissue grafts attached to the at least one suture anchor within the glenoid defect. The suture anchors can be knotted or knotless, or a combination of knotted and knotless. The method can further include the steps of: folding (one or multiple times) at least one of the one or more soft tissue grafts; and securing the folded soft tissue into the glenoid defect. The method can further include the step of attaching glenoid native tissue to the glenoid. The method can further include the steps of: passing sutures from the at least one suture anchor through glenoid native tissue; fixating the glenoid native tissue over the one or more soft tissue grafts fixated within the glenoid defect; and securing the sutures to hold the one or more soft tissue grafts and the glenoid native tissue in place.

Referring now to the drawings, where like elements are designated by like reference numerals, FIGS. 1-9 illustrate exemplary glenoid repairs 100, 200, 300, 400, 500 (surgical repairs 100, 200, 300, 400, 500; soft tissue glenoid repairs 100, 200, 300, 400, 500; soft tissue glenoid augmentation repairs 100, 200, 300, 400, 500) with soft tissue glenoid repair systems 101, 201, 301, 401, 501 (systems 101, 201, 301, 401, 501; soft tissue/anchor glenoid systems 101, 201, 301, 401, 501; glenoid augmentation systems 101, 201, 301, 401, 501). The repairs and constructs detailed below include soft tissue grafts that can be used with either knotted or knotless suture anchors, or combination of knotted and knotless suture anchors.

FIG. 1 illustrates exemplary repair 100 with two soft tissue grafts 21 secured within the glenoid defect 91 of glenoid 90. Exemplary soft tissue grafts 21 are delivered to the glenoid defect 91 (illustrated more clearly in FIGS. 2 and 3) with flexible strands 55, 65 attached to fixation devices 50, 60. Fixation devices 50, 60 can be suture anchors. Fixation devices 50, 60 can be knotted or knotless. Repair 101 illustrates exemplary knotted fixation device 50 and exemplary knotless fixation device 60; however, the disclosure contemplates any number of knotted and knotless fixation devices, depending on the characteristics of each surgical procedure and as desired.

FIG. 1 also illustrates native soft tissue 80 placed over top of soft tissue grafts 21 to repair the native soft tissue 80 into its anatomical position. Native soft tissue 80 can be placed and fixated over the soft tissue graft by employing flexible strands 55, 65 from fixation devices 50, 60 which are passed through the native tissue 80 and fixated on top of the repair. Fixation of flexible strands passed through the native soft tissue 80 on top of the glenoid repair can be achieved by using additional fixation devices, for example, additional knotless suture anchors.

Figure 2:
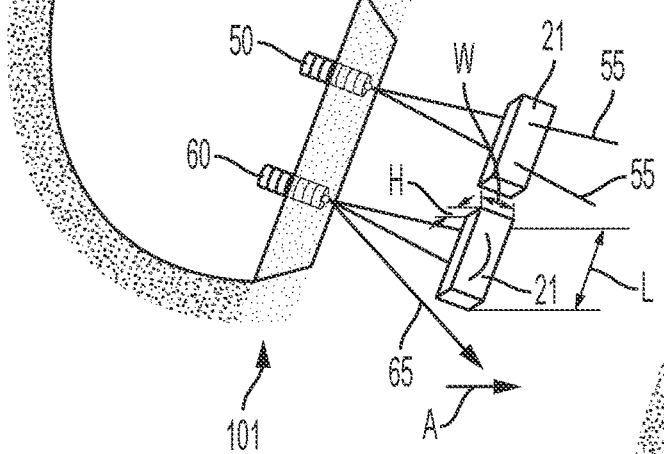
FIGS. 2 and 3 illustrate the glenoid augmentation with the soft tissue graft of FIG. 1 at intermediate stages of repair.
Figure 3:
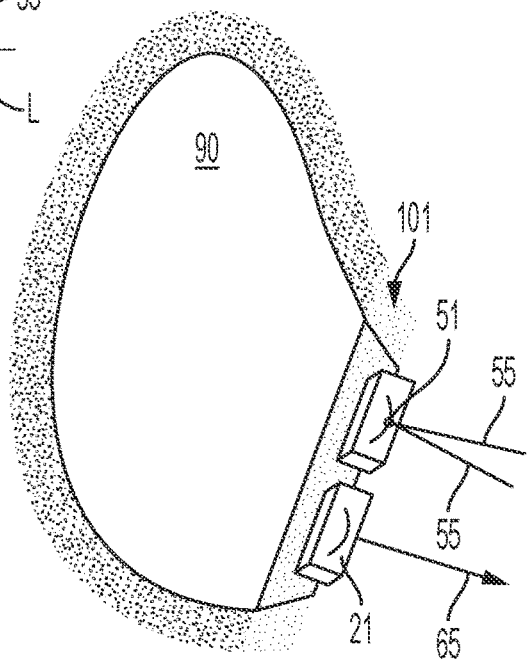

FIGS. 2 and 3 illustrate subsequent steps of glenoid augmentation with exemplary construct 101 to achieve the repair 100 of FIG. 1. Surgical construct 101 includes at least one soft tissue graft 21 and at least one fixation device 50, 60, for example, suture anchors 50, 60 that can be knotted or knotless anchors. For simplicity, FIGS. 1-3 illustrate a knotted fixation device 50 and a knotless fixation device 60, and only two soft tissue grafts 21. Fixation devices 50, 60 deliver and fixate soft tissue grafts 21 within glenoid defect 91. Fixation devices 50, 60 are inserted into the glenoid defect 91 and their flexible strands 55, 65 (sutures 55, 65) are passed through appropriately sized soft tissue grafts 21, as shown in FIG. 2.

Soft tissue grafts 21 each have a graft length, width and thickness that can vary depending on the size of the defect 91. Soft tissue grafts 21 can be provided in any number and each can have similar or different properties from the remaining grafts. The soft tissue grafts can be any soft tissue graft such as allograft, autograft, or synthetic graft, or combinations thereof. In an exemplary embodiment, body 10 of soft tissue graft 21 (FIG. 2) is a cuboid block with a length L, a width W, a height H and a center (FIG. 2), having exemplary dimensions of about 1×0.5×0.5 cm, dimensions which allow the graft to be introduced via the rotator interval and rest on the surface 92 of glenoid defect 91.

FIG. 3 shows placement of soft tissue grafts 21 over surface 92 of the defect 91. Flexible strands 55, 65 (sutures 55, 65) are passed through corresponding soft tissue grafts 21. The passed flexible strands 55, 65 (sutures 55, 65) are then used to deliver the soft tissue grafts 21 onto the defect 91. Flexible strands 55, 65 (sutures 55, 65) are then either tied or knotlessly fixated to hold the graft. For example, flexible strands 55 from knotted suture anchor 50 form knot 51 on top of one of the two soft tissue grafts 21, while flexible strand 65 from knotless suture anchor 60 extends from the other of the two soft tissue grafts 21 after securing the other of the two soft tissue grafts 21 within the defect 91. The remaining lengths of flexible strands 55, 65 (sutures 55, 65) can then be passed through the native tissue 80 (FIG. 1) and fixated over the top of the repair using additional knotless suture anchors.

Surface 92 is about perpendicular to the face of the glenoid 90 and defines the 3-D glenoid bone loss defect 91. Glenoid 90 is augmented using soft tissue graft 21 to provide stability to the shoulder joint. Suture anchors 50, 60 deliver and fixate the graft within the defect. Native soft tissue 80 can be subsequently repaired over top surface of the graft 21 into its anatomical position.

Figure 4:
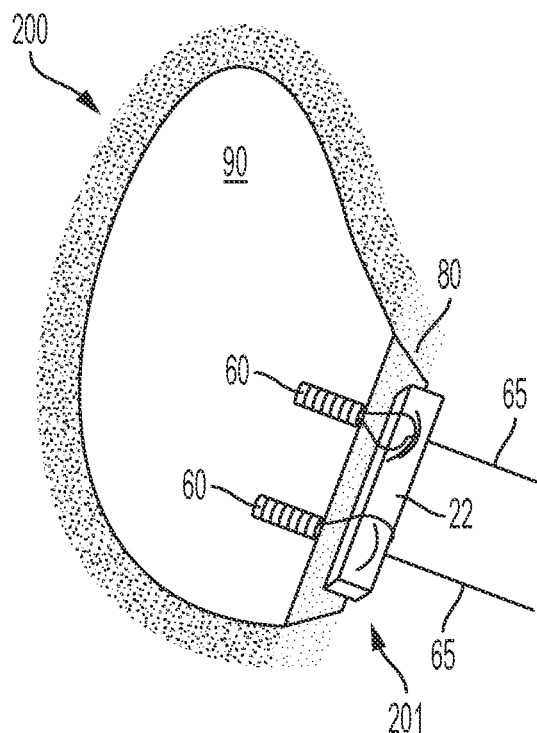
FIG. 4 illustrates another exemplary glenoid augmentation with soft tissue graft.
Figure 5:
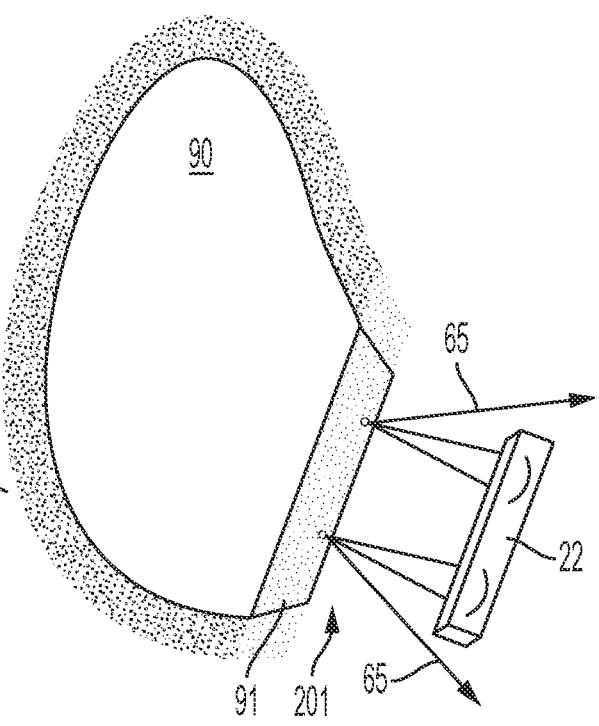
FIG. 5 illustrates the glenoid augmentation with the soft tissue graft of FIG. 4 at an intermediate stage of repair.

FIGS. 4 and 5 illustrate exemplary glenoid augmentation repair 200 which is about similar to exemplary repair 100 detailed above but differs in that construct 201 includes a single soft tissue graft 22 in lieu of two soft tissue grafts 21. Soft tissue graft 22 is secured within the glenoid defect 91 of glenoid 90 with at least one fixation device, for example, two fixation devices 60 in the form of two exemplary knotless suture anchors 60. Multiple anchors can be used to deliver and fixate one larger graft 22 (unitary, integral graft 22) instead of multiple smaller grafts 21. Sutures 65 from knotless suture anchors 60 pass through the graft 22 and deliver and fixate the soft tissue graft 22 within the glenoid defect 91. Sutures 65 can then be passed through the native tissue 80 (FIG. 4) and fixated over the top of the native tissue by using, for example, additional knotless suture anchors.

Figure 6:
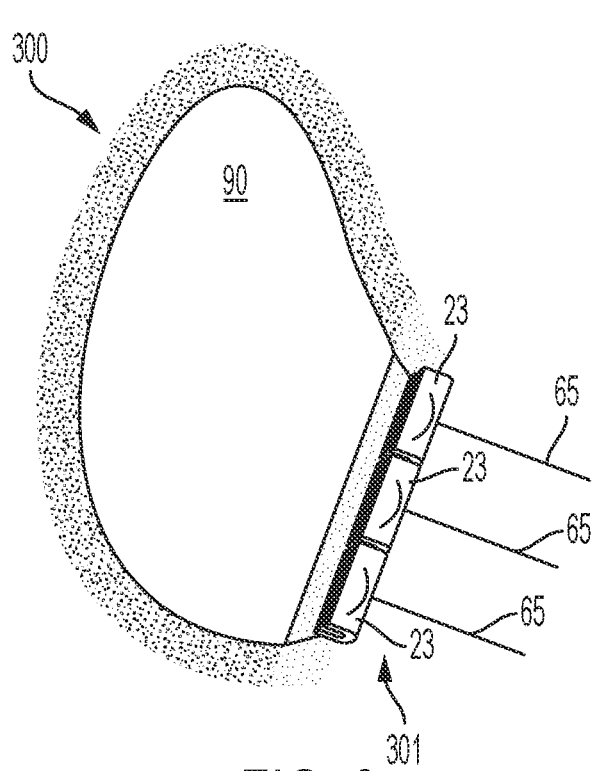
FIG. 6 illustrates another exemplary glenoid augmentation with soft tissue graft.
Figure 7:
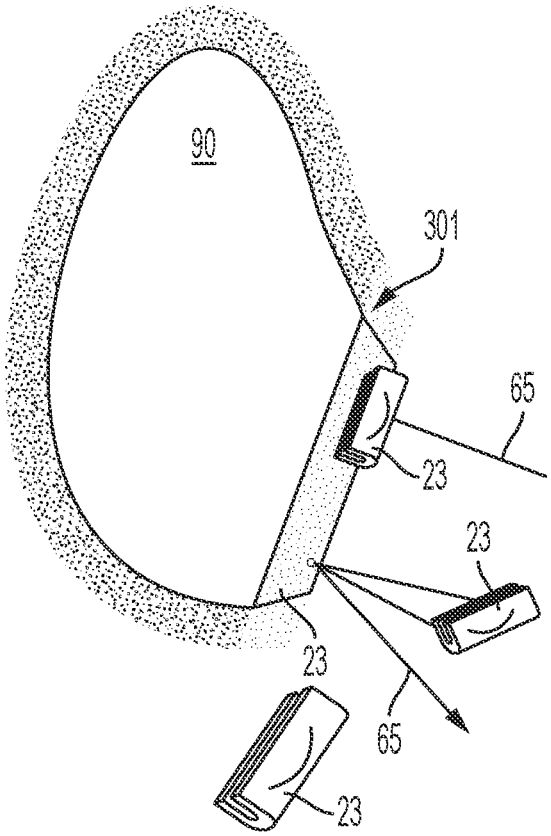
FIG. 7 illustrates the glenoid augmentation with the soft tissue graft of FIG. 6 at an intermediate stage of repair.

FIGS. 6 and 7 illustrate exemplary glenoid augmentation repair 300 which is about similar to exemplary repair 100 detailed above but differs in that construct 301 includes folded soft tissue grafts 23 to obtain a larger soft tissue thickness in the defect. Soft tissue grafts can be folded so as to position the ends of each graft together. Soft tissue grafts 23 are secured within the glenoid defect 91 of glenoid 90 with at least one fixation device, for example, three knotless suture anchors 60. Sutures 65 from knotless suture anchors 60 can be passed in the folded state to maintain this configuration during delivery and final fixation. Attachment of the sutures to the soft tissue grafts can be conducted intraoperatively. The grafts can be brought in and fixated together with one suture from a suture anchor or with sutures from separate suture anchors.

Figure 8:
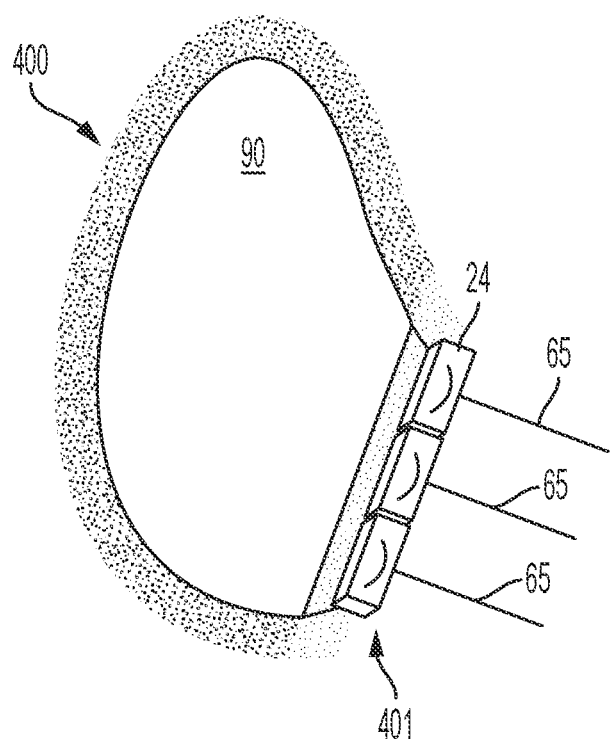
FIG. 8 illustrates another exemplary glenoid augmentation with soft tissue graft.
Figure 9:
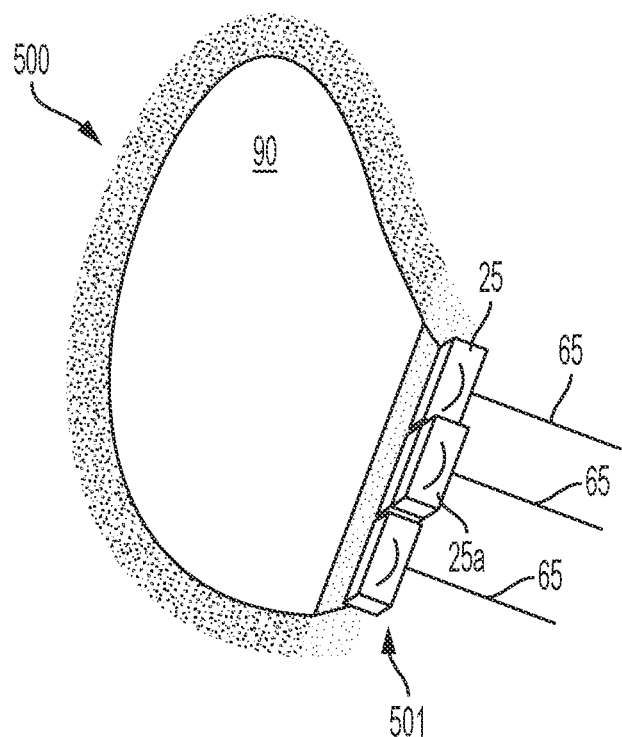
FIG. 9 illustrates another exemplary glenoid augmentation with soft tissue graft.

FIGS. 8 and 9 illustrate exemplary glenoid augmentation repairs 400, 500 which provide alternative options. Multiple folded and/or unfolded grafts can be used to fill defect 91. System 401 includes three exemplary small grafts 24 that are about equally sized and dimensioned. Grafts 24 completely fill the defect 91. System 501 of repair 500 includes multiple grafts 25, 25*a* stacked on top of each other to fill the defect. Soft tissue graft 25*a* is formed of two exemplary soft tissue grafts that are stacked on top of each other to augment the thickness of the repair 500. The grafts 24, 25, 25*a* can be brought in and fixated together with one suture from a suture anchor or with sutures from separate suture anchors. Like in the previously described embodiments, the remaining sutures can be passed through the native tissue 80 and then fixated over the top of the repair 300, 400, 500 using, for example, additional knotted or knotless suture anchors.

Although the embodiments above have been described with reference to soft tissue grafts filling up a glenoid bone loss defect, it must be understood that the disclosure also contemplates soft tissue grafts placed on a glenoid that has minimal bone loss or no bone loss at all, to achieve glenoid augmentation in cases where added glenoid stability is required. When minimal or no bone loss is present in the glenoid, the suture anchors and attached soft tissue grafts can be placed on the undamaged glenoid surface area requiring additional stability. Soft tissue grafts in conjunction with knotted and knotless suture anchors can be also employed for any bone loss that can be repaired/augmented with grafting.

A repair system 101, 201, 301, 401, 501 for glenoid augmentation includes a soft tissue graft 21, 22, 23, 24, 25, 25*a* and at least one fixation device 50, 60 attached to the soft tissue graft 21, 22, 23, 24, 25, 25*a*, wherein the at least one fixation device is secured into the glenoid 90 and the soft tissue graft is secured onto the glenoid 90. Soft tissue graft 21, 22, 23, 24, 25, 25*a* can be formed of a plurality of grafts (positioned one next to each other or stacked one on top of the other) or can be a unitary structure (a single, larger graft). Each of the plurality of grafts can have a shape and dimensions about equal to the shapes and dimensions of the others of the plurality of grafts. The at least one fixation device 50, 60 can be a knotted or knotless suture anchor. The at least one fixation device 50, 50 can be an "all suture anchor" or a soft suture anchor comprising a flexible tubular sleeve or sheath and a plurality of flexible strands extending through a passage of the flexible tubular sleeve or sheath. The soft tissue graft 21, 22, 23, 24, 25, 25*a* can partially or completely fill a glenoid bone loss 91. The soft tissue graft 21, 22, 23, 24, 25, 25*a* can be secured onto a glenoid surface of a glenoid 90 without bone loss.

A surgical kit for glenoid augmentation with soft tissue grafts can include one or more soft tissue grafts 21, 22, 23, 24, 25, 25*a* and one or more fixation devices (such as anchors 50, 60) attached to flexible members (such as sutures 55, 65). The one or more soft tissue grafts 21, 22, 23, 24, 25, 25*a* are used to fill into a glenoid bone defect, or to just simply augment the glenoid to provided added glenoid stability. The soft tissue grafts 21, 22, 23, 24, 25, 25*a* can be provided already attached to the flexible members 55, 65. The soft tissue grafts 21, 22, 23, 24, 25, 25*a* can be provided unattached to the flexible members 55, 65 so that attachment can be conducted intraoperatively. The surgical kit may include awls or equivalent devices, as well as drills or bone-penetrating devices. The surgical kit may also include a tensioner and/or additional fixation devices and associated instrumentation (if securement of the native ligament is also necessary).

Methods of surgeries are also disclosed. An exemplary method includes inter alia the steps of: (i) positioning one or more soft tissue grafts 21, 22, 23, 24, 25, 25*a* within a glenoid defect 91; and (ii) securing the one or more soft tissue grafts 21, 22, 23, 24, 25, 25*a* to the glenoid defect 91 with at least one suture anchor 50, 60. The method can further include the steps of: attaching the one or more soft tissue grafts 21, 22, 23, 24, 25, 25*a* to the at least one suture anchor 50, 60; inserting the at least one suture anchor 50, 60 attached to the soft tissue grafts 21, 22, 23, 24, 25, 25*a* into the glenoid 90; and delivering and fixating the one or more soft tissue grafts 21, 22, 23, 24, 25, 25*a* attached to the at least one suture anchor 50, 60 within the glenoid defect 91. The suture anchors 50, 60 can be knotted or knotless, or a combination of knotted and knotless. The method can further include the steps of: folding (one or multiple times) at least one of the one or more soft tissue grafts 21, 22, 23, 24, 25, 25*a*; and securing the folded soft tissue 21, 22, 23, 24, 25, 25*a* into the glenoid defect 91. The method can further include the step of attaching glenoid native tissue 80 to the glenoid 90. The method can further include the steps of: passing sutures 55, 65 from at least one suture anchor 50, 60 through glenoid native tissue 80; fixating the glenoid native tissue 80 over the one or more soft tissue grafts 21, 22, 23, 24, 25, 25*a*; and securing the sutures 55, 65 over the repair 100, 200, 300, 400, 500 to hold the one or more soft tissue grafts 21, 22, 23, 24, 25, 25*a* and the glenoid native tissue 80 in place.

Another exemplary method includes inter alia the steps of: (i) positioning one or more soft tissue grafts 21, 22, 23, 24, 25, 25*a* onto a glenoid 90 having minimal or no bone loss; and (ii) securing the one or more soft tissue grafts 21, 22, 23, 24, 25, with at least one suture anchor 50, 60. The method can further include the steps of: attaching the one or more soft tissue grafts 21, 22, 23, 24, 25, 25*a* to the at least one suture anchor 50, 60; inserting the at least one suture anchor 50, 60 attached to the soft tissue grafts 21, 22, 23, 24, 25, 25*a* into the glenoid 90; and delivering and fixating the one or more soft tissue grafts 21, 22, 23, 24, 25, 25*a* attached to the at least one suture anchor 50, 60 to the glenoid. The suture anchors 50, 60 can be knotted or knotless, or a combination of knotted and knotless. The method can further include the steps of: passing sutures 55, 65 from the suture anchor 50, 60 through the one or more soft tissue grafts 21, 22, 23, 24, 25, 25*a*; pulling on the sutures 55, 65 to bring the one or more soft tissue grafts 21, 22, 23, 24, 25, 25*a* onto the glenoid; and securing the soft tissue 21, 22, 23, 24, 25, 25*a* onto the glenoid. The method can further include the steps of: folding (one or multiple times) at least one of the one or more soft tissue grafts 21, 22, 23, 24, 25, 25*a*; and securing the folded soft tissue 21, 22, 23, 24, 25, 25*a* onto the glenoid. The method can further include the steps of: passing sutures 55, 65 from at least one suture anchor 50, 60 through glenoid native tissue 80; fixating the glenoid native tissue 80 over the one or more soft tissue grafts 21, 22, 23, 24, 25, 25*a* fixated to the glenoid 90; and securing the sutures 55, 65 with additional fixation devices, such as additional suture anchors.

Soft tissue grafts 21, 22, 23, 24, 25, 25*a* can be any soft tissue replacement or soft tissue replacement materials. Soft tissue grafts 21, 22, 23, 24, 25, 25*a* may be allograft, autograft, xenograft or artificial graft material. In an exemplary embodiment, at least one of soft tissue grafts 21, 22, 23, 24, 25, 25a can be an intraoperatively or preoperatively harvested tendon such as hamstring (especially semitendinosus). Soft tissue grafts 21, 22, 23, 24, 25, 25a can be dimensioned to be folded one or more times, if desired and necessary, and/or to be stacked one on top of the other. Soft tissue gratis 21, 22, 23, 24, 25, 25a can be folded one to several times to alter the shape of the total graft construct. Soft tissue grafts 21, 22, 23, 24, 25, 25a can be dimensioned to also follow the contour of the glenoid bone loss defect and/or the glenoid rim so that the soft tissue grafts that fill the defect or that simply augment the glenoid do not extend laterally beyond the glenoid rim. Soft tissue grafts 21, 22, 23, 24, 25, 25a can allow native labrum to be tied down to the soft tissue grafts 21, 22, 23, 24, 25, 25a; the labrum will contact the glenoid to keep it in place and add security and increased fixation.

The soft tissue repairs 100, 200, 300, 400 can employ at least one knotless and/or knotted fixation device 50, 60. The knotless fixation devices can be knotless anchors, for example, swivel and/or screw-in suture anchors and/or push-in anchors (such as an Arthrex SwiveLock® anchor or a PushLock® Anchor). In an exemplary embodiment, the fixation device is a knotless suture anchor such as the two-piece Arthrex PushLock® anchor, disclosed in U.S. Pat. No. 7,329,272, or an Arthrex SwiveLock® anchor, disclosed in U.S. Pat. No. 8,012,174 issued Sep. 6, 2011, and U.S. Pat. No. 9,005,246 issued Apr. 14, 2015, the disclosures of all of which are fully incorporated by reference in their entirety herein. In an exemplary embodiment, the fixation device 50, 60 is an all-suture soft anchor (soft suture anchor) provided with a soft anchor sleeve (sheath, tubular member) with two open ends and one or more flexible shuttling strands extending through the soft anchor sleeve (sheath). The at least two flexible strands may extend through the sleeve in similar or different directions and/or orientations and/or locations. The flexible sleeve with the one or more shuttling strands is secured into or onto bone (glenoid), and the strands allow passing of additional flexible strands such as tapes to pass over soft tissue and be secured into bone to approximate soft tissue to bone. Details of an exemplary soft suture anchor with a soft anchor sleeve (sheath or tubular member) and flexible shuttling strands are set forth, for example, in U.S. application Ser. No. 15/998,516 entitled "Methods of Tissue Repairs" filed on Aug. 16, 2018, the disclosure of which is incorporated by reference in its entirety herein.

Flexible strands 55, 65 can be high strength suture, tape, suture tape, combination of suture and tape, wire, cable, weave, mesh, ribbon, textile or fabric, or combinations thereof, among many others. Flexible strands 55, 65 can be a round suture or a suture tape, or combination thereof. Flexible strands 55, 65 can be made of any known suture construct, such as multifilament, braided, knitted, woven suture, or including fibers of ultrahigh molecular weight polyethylene (UHMWPE). Flexible strands 55, 65 can consist of, or consist essentially of, suture. Flexible strands 55, 65 can be formed of a high strength suture material such as FiberWire® suture, sold by Arthrex, Inc. of Naples, Fla., and described in U.S. Pat. No. 6,716,234, the disclosure of which is incorporated by reference herein. FiberWire® suture is formed of an advanced, high-strength fiber material, namely ultrahigh molecular weight polyethylene (UHMWPE), sold under the tradenames Spectra® (Honeywell International Inc., Colonial Heights, Va.) and Dyneema® (DSM N.V., Heerlen, the Netherlands), braided with at least one other fiber, natural or synthetic, to form lengths of suture material.

Flexible strands 55, 65 can be braided or multi-filament suture such as FiberTape® suture tape (as disclosed in U.S. Pat. No. 7,892,256, the disclosure of which is incorporated in its entirety herewith) or collagen tape, or wide "tape like" material, or combinations thereof.

Flexible strands 55, 65 can consist essentially of suture or suture material, or combination of suture and other materials such as long chain synthetic polymers like polyester and nylon, or materials such as PET, silk nylon or absorbable polymers, or coating materials (such as wax, silk, or silicone products), among many others. Flexible strands 55, 65 can consist of strands with cross-sections of various forms and geometries, including round, oval, rectangular, or flat, among others, or combinations of such forms and geometries. In an embodiment, at least one of flexible strands 55, 65 can be provided as a suture which is braided, knitted or woven. Flexible strands 55, 65 can be absorbable or non-absorbable, or partially absorbable.

Flexible strands 65 can be also formed of a stiff material, or combination of stiff and flexible materials, depending on the intended application. Flexible strands 55, 65 can be also coated and/or provided in different colors. In an embodiment, parts (or all) of construct 101, 201, 301, 401, 501 can be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture and/or tape, pliability, handleability or abrasion resistance, for example.

Flexible strands 55, 65 can be also provided with tinted tracing strands, or otherwise contrast visually with other parts of the construct, which remain a plain, solid color, or displays a different tracing pattern, for example. Various structural elements of surgical construct 101, 201, 301, 401, 501 may be visually coded, making identification and handling of the suture legs simpler. Easy identification of suture in situ is advantageous in surgical procedures.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A repair system for glenoid augmentation, comprising:
   one or more soft tissue grafts placed within a glenoid bone loss defect, wherein the one or more soft tissue grafts are dimensioned to follow a contour of the glenoid bone loss defect and to fill the glenoid bone loss defect, wherein at least one of the one or more soft tissue grafts is folded at least once; and
   at least one fixation device attached to the one or more soft tissue grafts, wherein the at least one fixation device is secured into the glenoid and the one or more soft tissue grafts are secured onto the glenoid.

2. The repair system of claim 1, wherein the one or more soft tissue grafts are formed of a plurality of grafts.

3. The repair system of claim 2, wherein each of the plurality of grafts has a shape and dimensions about equal to shapes and dimensions of the others of the plurality of grafts.

4. The repair system of claim 2, wherein one of the plurality of grafts has a thickness greater than thicknesses of the others of the plurality of grafts.

5. The repair system of claim 1, wherein the at least one fixation device is a knotted or knotless suture anchor.

6. The repair system of claim 1, wherein the at least one fixation device is a soft suture anchor comprising a flexible tubular sleeve or sheath and a plurality of flexible strands extending through a passage of the flexible tubular sleeve or sheath.

7. The repair system of claim 1, wherein the one or more soft tissue grafts completely fills a glenoid bone loss.

8. The repair system of claim 1, wherein the one or more soft tissue grafts are in the form of a cuboid block.

* * * * *